United States Patent [19]

Powell et al.

[11] Patent Number: 5,786,524
[45] Date of Patent: Jul. 28, 1998

[54] PROCESS FOR PREPARATION OF 1,3-PROPANEDIOL VIA HYDROGENATION OF 3-HYDROXYPROPANAL

[75] Inventors: Joseph Broun Powell, Houston; William Ridley Pledger, Pearland; Andreas Nikolaos Matzakos, Missouri City; Paul Richard Weider, Houston; Juan Pedro Arhancet, Katy, all of Tex.

[73] Assignee: Shell Oil Company, Houston, Tex.

[21] Appl. No.: 655,639

[22] Filed: May 30, 1996

[51] Int. Cl.⁶ .................. C07C 31/18; C07C 27/04
[52] U.S. Cl. ............................. 568/862; 568/852
[58] Field of Search ................... 568/852, 862; 502/301, 326

[56] References Cited

U.S. PATENT DOCUMENTS

| | | | |
|---|---|---|---|
| 3,687,981 | 8/1972 | Lawrence et al. | 260/340.7 |
| 5,015,789 | 5/1991 | Arntz et al. | |
| 5,256,827 | 10/1993 | Slaugh et al. | |
| 5,304,686 | 4/1994 | Slaugh . | |
| 5,334,778 | 8/1994 | Haas et al. | 568/862 |
| 5,364,984 | 11/1994 | Arntz et al. | 568/862 |
| 5,576,471 | 11/1996 | Semple . | |

FOREIGN PATENT DOCUMENTS

96/10552  4/1996  WIPO .

OTHER PUBLICATIONS

Valerius et al., "Modelling of a trickle–bed reactor II. The hydrogenation of 3–hydroxypropanal to 1,3–propanediol", *Chemical Eng. and Proc.*, 35, pp. 11–19 (1996).
Patent Search Report of 24 Sep. 1997.

*Primary Examiner*—Gary Geist
*Assistant Examiner*—Karl J. Puttlitz

[57] ABSTRACT

1,3-propanediol is prepared from 3-hydroxypropanal in a process comprising the steps of:

(a) contacting, at a temperature within the range of about 50° to about 100° C. and a pressure within the range of about 500 to about 5000 psig, ethylene oxide with carbon monoxide and hydrogen in an essentially non-water-miscible solvent in the presence of an effective amount of a non-phosphine-ligated cobalt or rhodium catalyst and an effective amount of a catalyst promoter under reaction conditions effective to produce an intermediate product mixture comprising less than 15 wt % 3-hydroxypropanal;

(b) adding an aqueous liquid to said intermediate product mixture and extracting into said aqueous liquid a major portion of the 3-hydroxypropanal at a temperature less than about 100° C. so as to provide an aqueous phase comprising 3-hydroxypropanal in a concentration of at least about 20 wt %, and an organic phase comprising at least a portion of the cobalt or rhodium catalyst or a cobalt- or rhodium-containing derivative thereof;

(c) separating the aqueous phase from the organic phase;

(d) diluting the aqueous phase comprising 3-hydroxypropanal with an aqueous liquid to form a 3-hydroxypropanal solution having a 3-hydroxypropanal concentration within the range of about 0.2 to about 15 weight percent;

(e) passing said aqueous 3-hydroxypropanal solution to a hydrogenation zone and in contact with a fixed-bed hydrogenation catalyst under hydrogenation conditions for a time effective to form an aqueous solution comprising 1,3-propanediol; and (f) recovering said 1,3-propanediol.

9 Claims, 1 Drawing Sheet

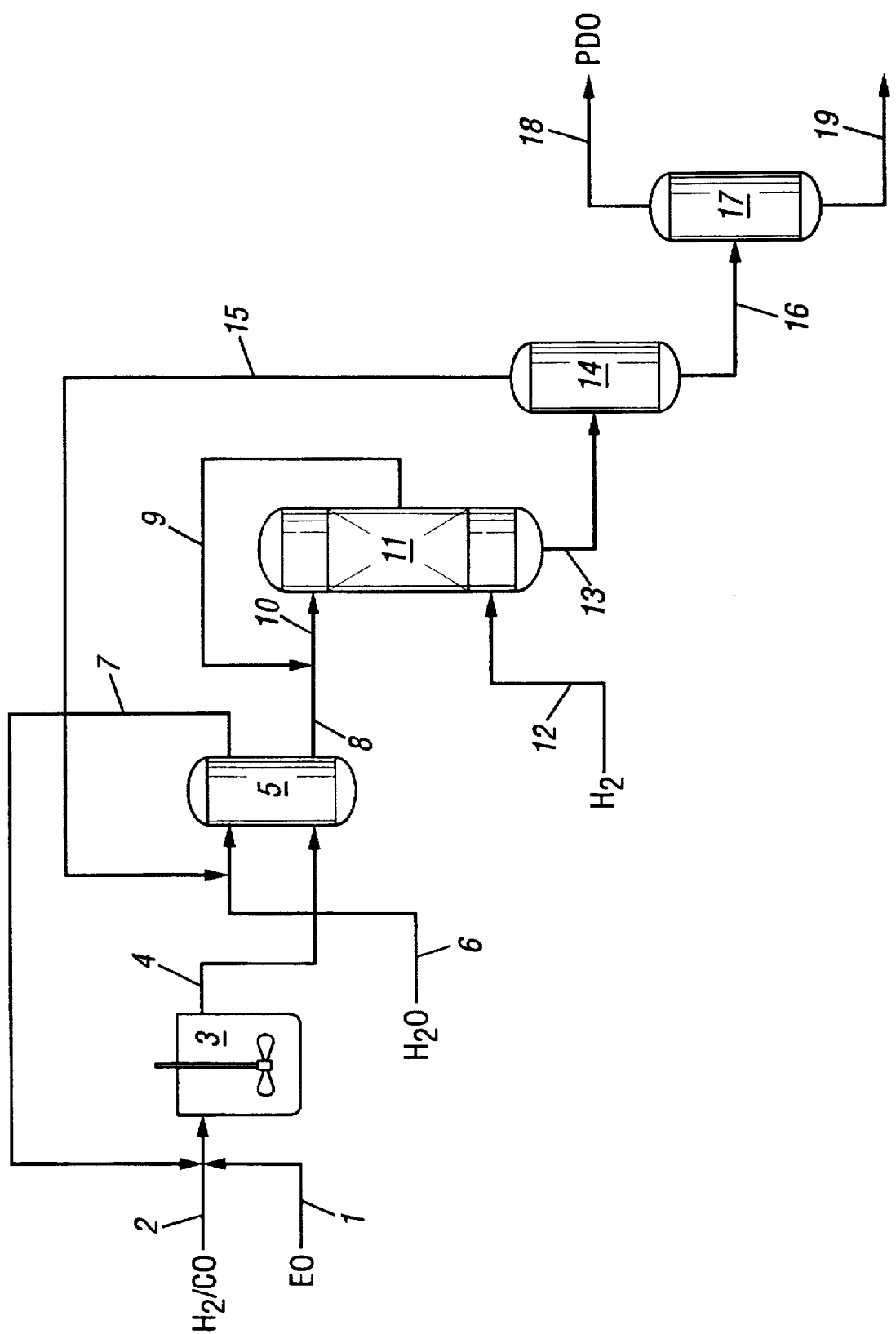

PROCESS FOR PREPARATION OF 1,3-PROPANEDIOL VIA HYDROGENATION OF 3-HYDROXYPROPANAL

BACKGROUND OF THE INVENTION

This invention relates to the preparation of 1,3-propanediol. In a specific aspect, the invention relates to the preparation of 1,3-propanediol from ethylene oxide via hydrogenation of 3-hydroxypropanal.

1,3-propanediol (PDO) is an intermediate in the production of polyesters for fibers and films. It is known to prepare PDO in a process involving (1) the cobalt-catalyzed hydroformylation (reaction with synthesis gas, $H_2/CO$) of ethylene oxide to prepare a dilute solution of intermediate 3-hydroxypropanal (HPA); (2) extraction of the HPA into water to form a more concentrated HPA solution; and (3) hydrogenation of the HPA to PDO.

For process economics, it is important for the HPA hydrogenation step to be highly selective to PDO. Selectivity is, however, complicated by the high reactivity of HPA, which can react with species in the hydrogenation reaction mixture to form by-products which lower product yield and complicate product recovery. It is known to improve selectivity by using a slurry catalyst at relatively low temperatures between 60° and 90° C. Slurry catalyst systems are, however, quite costly to operate.

It would therefore be desirable to prepare PDO from HPA with high selectivity in a relatively inexpensive fixed-bed catalyst system.

It is therefore an object of the invention to provide a selective process for the preparation of 1,3-propanediol from ethylene oxide via intermediate 3-hydroxypropanal using a fixed-bed hydrogenation catalyst.

SUMMARY OF THE INVENTION

According to the invention, 1,3-propanediol is prepared in a process comprising the steps of:

(a) contacting, at a temperature within the range of about 50° to about 100° C. and a pressure within the range of about 500 to about 5000 psig, ethylene oxide with carbon monoxide and hydrogen in an essentially non-water-miscible solvent in the presence of an effective amount of a non-phosphine-ligated cobalt or rhodium catalyst and an effective amount of a catalyst promoter under reaction conditions effective to produce an intermediate product mixture comprising less than 15 wt % 3-hydroxypropanal;

(b) adding an aqueous liquid to said intermediate product mixture and extracting into said aqueous liquid a major portion of the 3-hydroxypropanal at a temperature less than about 100° C. so as to provide an aqueous phase comprising 3-hydroxypropanal in a concentration of at least about 20 wt %, and an organic phase comprising at least a portion of the cobalt or rhodium catalyst or a cobalt- or rhodium-containing derivative thereof;

(c) separating the aqueous phase from the organic phase;

(d) diluting said aqueous phase with an aqueous liquid to form a 3-hydroxypropanal solution having a 3-hydroxypropanal concentration within the range of about 0.2 to about 15 weight percent;

(e) passing said aqueous 3-hydroxypropanal solution to a hydrogenation zone and in contact with a fixed-bed hydrogenation catalyst under hydrogenation conditions to form an aqueous 1,3-propanediol; and (f) recovering said 1,3-propanediol.

In a specific embodiment of this process, dilution of the relatively concentrated 3-hydroxypropanal solution is effected with an aqueous 1,3-propanediol solution passed to the 3-hydroxypropanal solution from downstream hydrogenation. Dilution of this aqueous 3-hydroxypropanal solution prior to hydrogenation permits the use of a relatively inexpensive fixed-bed hydrogenation catalyst without sacrificing hydrogenation selectivity. Use of an aqueous solution of 1,3-propanediol to dilute the 3-hydroxypropanal solution further enhances selectivity and yields of 1,3-propanediol, prolongs catalyst life, and saves on equipment and cooling costs.

BRIEF DESCRIPTION OF THE DRAWING

The FIGURE is a schematic flow diagram of one embodiment of the invention 1,3-propanediol preparation process.

DETAILED DESCRIPTION OF THE INVENTION

The invention can be conveniently described by reference to the FIGURE, which illustrates an embodiment of the invention process for preparation of 1,3-propanediol by hydroformylation of ethylene oxide to 3-hydroxypropanal and then hydrogenation of the 3-hydroxypropanal to 1,3-propanediol.

In the illustrated embodiment, separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a hydroformylation catalyst, generally a metal carbonyl selected from rhodium and cobalt carbonyls. The hydroformylation catalyst will generally be present in the reaction mixture in an amount within the range of about 0.01 to about 1 wt %, preferably about 0.05 to about 0.3 wt %, based on the weight of the hydroformylation reaction mixture. The hydrogen and carbon monoxide will generally be introduced into the reaction vessel in a molar ratio within the range of about 1:2 to about 8:1, preferably about 1:1 to about 6:1.

The hydroformylation reaction is carried out under conditions effective to produce a hydroformylation reaction product mixture containing a major portion of 3-hydroxypropanal and a minor portion of acetaldehyde and 1,3-propanediol, while maintaining the level of 3-hydroxypropanal in the reaction mixture at less than 15 wt %, preferably within the range of about 5 to about 10 wt %. (To provide for solvents having different densities, the desired concentration of 3-hydroxypropanal in the reaction mixture can be expressed in molarity, i.e., less than 1.5M, preferably within the range of about 0.5 to about 1M.) Generally, the cobalt-catalyzed hydroformylation reaction is carried out at elevated temperature less than 100° C., preferably about 60° to about 90° C., most preferably about 75° to about 85° C., with rhodium-catalyzed hydroformylations on the order of about 10° C. higher. The hydroformylation reaction is generally carried out at a pressure within the range of about 100 to about 5000 psig, preferably (for process economics) about 1000 to about 3500 psig, with higher pressures preferred for greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 90° C. ) and relatively short residence times (about 20 minutes to about 1 hour) are preferred.

The hydroformylation reaction is carried out in a liquid solvent inert to the reactants. By "inert" is meant that the solvent is not consumed during the course of the reaction. In general, ideal solvents for the hydroformylation process will solubilize carbon monoxide, will be essentially non-watermiscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %, so as to form a separate hydrocarbon-rich phase upon water extraction of 3-hydroxypropanal from the hydroformylation reaction mixture. Preferably this solubility is less than 10%, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula

$$R_2-O-R_1 \quad (1)$$

in which $R_1$ is hydrogen or $C_{1-20}$ linear, branched, cyclic or aromatic hydrocarbyl or mono- or polyalkylene oxide, and $R_2$ is $C_{1-20}$ linear, branched, cyclic or aromatic hydrocarbyl, alkoxy or mono- or polyalkylene oxide. The most preferred hydroformylation solvents can be described by the formula

$$R_4-C(R_3)(R_5)-O-R_1 \quad (2)$$

in which $R_1$ is hydrogen or $C_{1-8}$ hydrocarbyl, and $R_3$, $R_4$ and $R_5$ are independently selected from $C_{1-8}$ hydrocarbyl, alkoxy and alkylene oxide. Such ethers include, for example, methyl-t-butyl ether, ethyl-t-butyl ether, diethyl ether, phenylisobutyl ether, ethoxyethyl ether, diphenyl ether and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of 3-hydroxypropanal which can be achieved under moderate reaction conditions, is methyl-t-butyl ether.

To further enhance yields under moderate reaction conditions, the hydroformylation reaction mixture will preferably include a catalyst promoter to accelerate the reaction rate. Suitable promoters include sources of mono- and multivalent metal cations of weak bases such as alkali, alkaline earth and rare earth metal salts of carboxylic acids. Also suitable are lipophilic promoters such as lipophilic phosphonium salts and lipophilic amines, which accelerate the rate of hydroformylation without imparting hydrophilicity (water solubility) to the active catalyst. As used herein, "lipophilic" means that the promoter tends to remain in the organic phase after extraction of 3-hydroxypropanal with water. The promoter will generally be present in an amount within the range of about 0.01 to about 1.0 mole per mole of cobalt. Suitable metal salts include sodium, potassium and cesium acetates, propionates and octoates; calcium carbonate and lanthanum acetate. The currently preferred lipophilic promoters are tetrabutylphosphonium acetate and dimethyldodecyl amine.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butyl ether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the catalyst and a minor amount of reaction by-products, is cooled and passed to extraction vessel 5, wherein an aqueous liquid, generally water and optional miscibilizing solvent, are added via 6 for extraction and concentration of the 3-hydroxypropanal for the subsequent hydrogenation step. Liquid extraction can be effected by any suitable means, such as mixer-settlers, packed or trayed extraction columns, or rotating disk contactors. Extraction can, if desired, be carried out in multiple stages. The amount of water added to the hydroformylation reaction product mixture will generally be such as to provide a water:mixture ratio within the range of about 1:1 to about 1:20, preferably about 1:5 to about 1:15. Water extraction is preferably carried out at a temperature within the range of about 25° to about 55° C., with lower temperatures preferred. Water extraction under 50 to 200 psig carbon monoxide at 25° to 55° C. maximizes catalyst recovery in the organic phase.

The organic phase containing the reaction solvent and the major portion of the cobalt catalyst can be recycled, with optional purge of heavy ends, from the extraction vessel to hydroformylation reaction via 7. Aqueous extract 8 can optionally be subjected to additional operations, such as passage through an acid ion exchange resin bed, re-extraction with a non-water-miscible solvent, complete or partial oxidation of cobalt followed by precipitation and filtration, deposition on a solid support, or extraction using a non-water-miscible solvent for removal of residual cobalt catalyst. Aqueous extract 8 is passed to hydrogenation zone 11 and reacted with hydrogen 12 in the presence of a hydrogenation catalyst to produce a hydrogenation product mixture 13 containing 1,3-propanediol.

In accordance with the invention process, input stream 10 to hydrogenation vessel 11 is an aqueous solution containing 3-hydroxypropanal in a concentration within the range of about 0.2 to about 15 wt %, preferably about 0.3 to about 8 wt %, based on the weight of the aqueous liquid. In the embodiment shown, outlet stream 8 from aqueous extraction of the hydroformylation product contains 3-hydroxypropanal in greater concentration (generally about 20 to about 40 wt %) than that desired for selective hydrogenation. Dilution is accomplished by addition of an aqueous liquid to this relatively concentrated 3-hydroxypropanal solution.

Although any aqueous liquid which will not interfere with hydrogenation of the 3-hydroxypropanal, including water, can be used for dilution of the 3-hydroxypropanal solution to the desired concentration, it is preferred to employ an aqueous 1,3-propanediol-containing solution such as hydrogenation output stream 9. Dilution with such a PDO-containing solution serves to concentrate PDO in the system water, thus avoiding the high cost of recovery of dilute PDO from water which would result from the use of water alone as the diluent. The preferred dilution stream will contain 1,3-propanediol and 3-hydroxypropanal in an amount within the range of about 20 to about 40 wt %, such as could be conveniently routed from an early stage of hydrogenation. The dilution stream 9 will preferably be cooled prior to admixture with the hydroformylation output stream to bring the temperature of the combined stream to that desired for input to the initial stage of hydrogenation.

In the illustrated embodiment, aqueous 1,3-propanediol stream 9 is used to dilute aqueous 3-hydroxypropanal stream 8. Other configurations of the hydrogenation input and recycle streams can be employed within the concept of the use of a 1,3-propanediol-containing stream for dilution of the 3-hydroxypropanal. For example, stream 8 can be divided for input into both a first hydrogenation catalyst bed and a second hydrogenation catalyst bed downstream from the first. The aqueous product stream passing from the first catalyst bed into the downstream second bed would serve to dilute the 3-hydroxypropanal feed into this second catalyst bed.

Hydrogenation of the aqueous 3-hydroxypropanal to 1,3-propanediol is carried out over a fixed-bed supported hydrogenation catalyst. The catalyst can be a Group VIII metal such as nickel, cobalt, ruthenium, platinum or palladium, as well as copper, zinc, chromium, and mixtures and alloys of these. The preferred catalysts are particulate nickel-based compositions on water-stable (e.g. ceramic) supports, such as are commercially available as Calsicat E-475SR (nickel on a ceramic support, 8×14 mesh spheres) and R-3142 from W. R. Grace. Particle size for the catalyst will be that consistent with fixed-bed operation, which will generally range from about 10 microns to about 3 mm, with larger particles giving lower pressure drop at the expense of activity.

The invention hydrogenation process can be carried out in one stage or in two or more sequential temperature stages. In a preferred embodiment, hydrogenation is carried out as described above at a temperature within the range of about 50° to about 130° C., followed by a second stage carried out at a temperature higher than that of the first stage and within the range of about 70° to about 155° C., and then optionally a third stage at a temperature greater than about 120° C. for reversion of heavy ends to 1,3-propanediol. In such a process, the illustrated hydrogenation zone 11 includes a series of two or more hydrogenation stages, optionally carried out in two or more separate reaction vessels. Dilution stream 9 is preferably output from the first hydrogenation stage. The preferred catalysts for the second-stage hydrogenation include nickel-based catalysts such as those referenced above for the first stage, as well as copper chromite or copper-zinc catalysts.

Residual solvent and extractant water can be recovered by distillation in column 14 and recycled via 15 to the water extraction process via a further distillation (not shown) for separation and purge of light ends. 1,3-Propanediol-containing product stream 16 can be passed to distillation column 17 for recovery of 1,3-propanediol 18 from heavy ends 19.

EXAMPLE 1

A series of hydrogenation experiments was performed in a 0.5-L autoclave reactor with agitation provided by a draft-tube gas dispersion impeller to enhance the rate of transport of hydrogen gas into the liquid phase. Approximately 28 g of a commercial 8/14-mesh spherical supported nickel catalyst (50 wt % nickel on silica/alumina, 0.43 ml/g pore volume) were retained in an annular catalyst basket to examine fixed-bed catalyst performance. The same catalyst was crushed under an inert atmosphere to give 1–20 micron particles for examination of slurry catalyst performance. For slurry studies, the crushed catalyst was added directly to the reactor in the absence of the catalyst basket. The reactor was charged with 300–350 ml of aqueous hydroformylation product rich in 3-hydroxypropanal (HPA) intermediate. The reactor was operated at 1000–1700 rpm agitation and 1000 psi hydrogen, which was replenished as depleted during the reaction. A filtered dip tube allowed sampling of the reactor to monitor the course of reaction. Samples were analyzed using a temperature-programmed capillary gas chromatograph to determine remaining HPA and 1,3-propanediol (PDO) formed.

Apparent selectivities were computed as moles of PDO formed per mole of HPA converted. Apparent selectivities in excess of 100% indicate reversion of heavy ends (formed during ethylene oxide hydroformylation) to PDO.

Runs 1–3 examined slurry catalyst performance. Hydrogenation activities (defined as the pseudo-first-order rate constant for consumption of HPA, assuming a first order dependence upon catalyst concentration) ranged from 96 to 233 l/h/wt.cat, with selectivities in excess of 100% at HPA concentrations up to 22 wt %.

Runs 4–7 examined particulate-form (8×14 mesh) catalyst at HPA concentrations from 18 to 23 wt %. For these runs, hydrogenation activities were reduced more than 10-fold relative to the slurry catalyst hydrogenation. Selectivity for the initial hydrogenation run was only 85%. The observed selectivity and activity diminished upon recycle of the catalyst, indicating degradation of catalyst performance.

Runs 8–11 examined performance of the particulate catalyst over a range of initial HPA concentrations. For these runs, HPA solutions were diluted with deionized water. (Separate runs demonstrated that dilution with PDO/water solutions gave equivalent results to dilution with water alone. Water dilution, however, gave more accurate product analysis than did dilution with PDO/water.) For the initial runs at dilute (2.9–3.3 wt %) HPA concentrations with fresh particulate catalyst (Run 8) and for the first recycle of this catalyst (Run 9), the hydrogenation activity remained essentially constant upon recycle, while selectivity remained at essentially 100%. With an increase in initial HPA concentration to 10.8 wt %, the hydrogenation activity sharply diminished. A further reduction in activity and a decrease in selectivity to 85% were observed upon increasing the initial HPA concentration to 21 wt % in the fourth cycle (Run 11).

For Runs 12–14, initial HPA concentrations were maintained below 4.5 wt %. Observed hydrogenation activities, although diminishing somewhat with catalyst recycle, remained high (at least equal to 50 l/h/wt.cat corrected to 70° C.), and selectivities remained over 100% for all runs.

TABLE 1

| Run | Reaction Temp., °C. | Initial HPA wt % | Grams Catalyst | Catalyst Form | Cycle | k (T) | k (70°C.) | Apparent PDO Selectivity |
|---|---|---|---|---|---|---|---|---|
| 1 | 60 | 17.32 | 5 | Crush sph | Fresh | 68.79 | 116.26 | 111 |
| 2 | 60 | 22.55 | 5 | Crush sph | Fresh | 137.87 | 233.00 | 102 |
| 3 | 80 | 3.04 | 7 | Crush sph | Fresh | 162.95 | 96.42 | 105 |
| 4 | 70 | 19.49 | 28 | Spheres | Fresh | 21.3 | 21.30 | 85 |
| 5 | 70 | 18.49 | 28 | Spheres | REC-1[1] | 7.77 | 7.77 | 66 |
| 6 | 70 | 23.35 | 28 | Spheres | REC-2 | 5.66 | 5.66 | 43 |
| 7 | 70 | 21.90 | 28 | Spheres | REC-3 | 3.3 | 3.30 | 53 |
| 8 | 70 | 3.31 | 28 | Spheres | Fresh | 36.24 | 36.24 | 99 |
| 9 | 70 | 2.93 | 28 | Spheres | REC-1 | 38.54 | 38.64 | 104 |
| 10 | 50 | 10.80 | 28 | Spheres | REC-2 | 6.69 | 19.11 | 106 |
| 11 | 50 | 21.16 | 28 | Spheres | REC-3 | 2.3 | 6.57 | 85 |
| 12 | 60 | 4.19 | 23 | Spheres | Fresh | 90.8 | 153.45 | 132 |
| 13 | 60 | 3.85 | 23 | Spheres | REC-1 | 40.44 | 66.34 | 122 |
| 14 | 60 | 3.51 | 23 | Spheres | REC-2 | 29.34 | 49.58 | 142 |

[1]REC = recycle

EXAMPLE 2

These experiments were performed to determine if an aqueous PDO solution could be used to dilute the hydrogenation input stream without adverse effects on hydrogenation activities.

Two batch hydrogenation reactions were carried out at 70° C. and 1000 psi using Calsicat E-475SR hydrogenation catalyst. In run A, a 28 wt % HPA concentrate produced by ethylene oxide hydroformylation and water extraction was diluted with deionized water to give an aqueous solution of 4.8 wt % HPA (with residual 0.2 wt % PDO). In run B, the HPA concentrate was diluted with purified PDO and water to give an aqueous solution of 3.9 wt % HPA and 24.4 wt % PDO. The observed hydrogenation activities were equivalent, within experimental error. Gas chromatographic analysis of product revealed no difference in by-product identity from the two hydrogenation reactions.

EXAMPLE 3

A series of experiments was conducted in a 500-ml autoclave reactor containing 28 g of the hydrogenation catalyst used in Example 2 and 300–325 g of HPA-containing aqueous feed. The aqueous feed was diluted with water to provide aqueous solutions containing between 3.8 and 4.8 wt % HPA. After pressure uptake (70° C., 1000 psi $H_2$) had been completed, liquid was drained from the reactor and replaced with fresh feed, to perform a recycle test of catalyst performance. Activities and selectivities for 9 recycles conducted in this manner using the diluted HPA solution were compared with those conducted under identical conditions using higher (19.5–21.9 wt %) HPA concentrations.

Use of a diluted HPA solution gave a higher intrinsic catalytic activity which stabilized at a higher value, compared with the recycle reactions using the more concentrated HPA solutions. Selectivity to PDO formation was greatly reduced with the undiluted feed and diminished with time. Excellent selectivities which did not diminish with time were observed with the diluted HPA solutions.

We claim:

1. A process for preparing 1,3-propanediol comprising the steps of:

(a) contacting, at a temperature within the range of about 50° to about 100° C. and a pressure within the range of about 500 to about 5000 psig, ethylene oxide with carbon monoxide and hydrogen in an essentially non-water-miscible solvent in the presence of an effective amount of a non-phosphine-ligated cobalt or rhodium catalyst and an effective amount of a catalyst promoter under reaction conditions effective to produce an intermediate product mixture comprising less than 15 wt % 3-hydroxypropanal;

(b) adding an aqueous liquid to said intermediate product mixture and extracting into said aqueous liquid a major portion of the 3-hydroxypropanal at a temperature less than about 100° C. so as to provide an aqueous phase comprising 3-hydroxypropanal in a concentration of at least about 20 wt %, and an organic phase comprising at least a portion of the cobalt or rhodium catalyst or a cobalt- or rhodium-containing derivative thereof;

(c) separating the aqueous phase from the organic phase;

(d) diluting said aqueous phase with an aqueous solution of 1,3-proganediol to form a 3-hydroxypropanal solution having a 3-hydroxypropanal concentration within the range of about 0.2 to about 15 weight percent;

(e) passing said aqueous 3-hydroxypropanal solution to a hydrogenation zone and in contact with a fixed-bed hydrogenation catalyst under hydrogenation conditions to form an aqueous solution comprising 1,3-propanediol; and (f) recovering said 1,3-propanediol.

2. The process of claim 1 in which the hydrogenation catalyst comprises nickel.

3. The process of claim 1 in which the concentration of 3-hydroxypropanal in the aqueous 3-hydroxypropanal solution passed to the hydrogenation zone is within the range of about 0.3 to about 8 wt %.

4. The process of claim 1 in which the dilution of step (d) is effected by adding an aqueous solution of 1,3-propanediol which has been produced by the hydrogenation process of step (e).

5. The process of claim 1 in which step (b) is carried out at a temperature within the range of about 50° to about 70° C.

6. The process of claim 1 in which step (e) further comprises passing the aqueous 1,3-hydroxypropanal solution to a first hydrogenation reactor and then to a second hydrogenation reactor maintained at a higher temperature than said first hydrogenation reactor.

7. The process of claim 1 in which the catalyst comprises nickel on a ceramic support.

8. The process of claim 1 in which step (d) further comprises forming the aqueous 3-hydroxypropanal solution by adding a sufficient quantity of an aqueous solution of 1,3-propanediol to form a dilute aqueous solution containing about 0.3 to about 12 weight percent of 3-hydroxypropanal.

9. A process for preparing 1,3-propanediol comprising the steps of:

(a) contacting ethylene oxide with carbon monoxide and hydrogen in an essentially non-water-miscible solvent in the presence of an effective amount of a non-phosphine-ligated cobalt catalyst and an effective amount of a catalyst promoter under reaction conditions effective to produce an intermediate product mixture comprising less than 15 wt % 3-hydroxypropanal;

(b) adding an aqueous liquid to said intermediate product mixture and extracting into said aqueous liquid a major portion of the 3-hydroxypropanal at a temperature less than about 100° C. so as to provide an aqueous phase comprising the 3-hydroxypropanal in greater concentration than the concentration of 3-hydroxypropanal in the intermediate product mixture, and an organic phase comprising at least a portion of the cobalt catalyst or a cobalt-containing derivative thereof;

(c) separating the aqueous phase from the organic phase;

(d) adding to said aqueous phase an aqueous solution of 1,3-propanediol to form a dilute aqueous 3-hydroxypropanal solution having a 3-hydroxypropanal concentration within the range of about 0.3 to about 12 weight percent;

(e) passing the dilute aqueous 3-hydroxypropanal solution to a hydrogenation zone containing a fixed-bed nickel hydrogenation catalyst maintained under hydrogenation conditions of temperature and pressure and therein converting at least a portion of the 3-hydroxypropanal to 1,3-propanediol; and (f) recovering the 1,3-propanediol.

* * * * *